United States Patent
Choy et al.

(10) Patent No.: US 6,329,515 B1
(45) Date of Patent: Dec. 11, 2001

(54) BIO-INORGANIC COMPOUND CAPABLE OF STABLE, SOLID-STATE STORAGE OF GENES AND PREPARATION THEREOF

(75) Inventors: Jin Ho Choy, Seoul National University, San 56-1, Shinlim-dong, Kwanak-Ku, Seoul 151-742; Seo Young Kwak; Jong Sang Park, both of Seoul, all of (KR)

(73) Assignee: Jin Ho Choy, Seoul (KR)

( * ) Notice: Subject to any disclaimer, the term of this patent is extended or adjusted under 35 U.S.C. 154(b) by 0 days.

(21) Appl. No.: 09/393,981

(22) Filed: Sep. 10, 1999

(30) Foreign Application Priority Data

Sep. 11, 1998 (KR) .................................................. 98-37497

(51) Int. Cl.$^7$ .......................... C07H 21/00; C07H 21/02; C07H 21/04
(52) U.S. Cl. .......................................... 536/23.1; 536/25.4
(58) Field of Search .................................... 536/23.1, 25.4

(56) References Cited

U.S. PATENT DOCUMENTS

| | | | |
|---|---|---|---|
| 5,187,260 | * | 2/1993 | Karali et al. .......................... 530/358 |
| 5,389,377 | * | 2/1995 | Chagnon et al. ..................... 424/450 |
| 5,441,746 | * | 8/1995 | Chagnon .............................. 424/450 |
| 5,935,866 | * | 8/1999 | Chagnon et al. ..................... 436/526 |

FOREIGN PATENT DOCUMENTS

| | | | |
|---|---|---|---|
| 0987328 | * | 3/2000 | (EP) . |
| 9218514 | * | 10/1992 | (WO) . |

OTHER PUBLICATIONS

Romanowski et al., "Plasmid DNA in a Groundwater Aquifer Microcosm—Adsorption, DNAase Resistance and Natural Genetic Transformations of Bacillus Subtilis,"*Molecular Ecology*, 2(3), 171–181 (1993); see also *Chemical Abstracts*, 120(11), p. 539, Abstract No. 129,352s (Mar. 14, 1994); Abstract supplied previously.*

Choy et al., "Intercalative Nanohybrids of Nucleoside Monophosphates and DNA in Layered Metal Hydroxide," *Journal of the American Chemical Society*, 121(6), 1399–1400 (Feb. 17, 1999).*

Atkári et al., "Interactions of Aluminum(III) with Phosphates," *Inorganic Chemistry*, 35(24), 7089–7094 (Nov. 20, 1996).*

Lovell et al., "Purification of DNA from Estuarine Sediments," *Journal of Microbiological Methods*, 20(3), 161–174 (Sep., 1994).*

Chamier et al., "Natural transformation of *Acinetobacter calcoaceticus* by Plasmid DNA Adsorbed on Sand and Grounwater Aquifer Material," *Applied and Environmental Microbiology*, 59(5), 1662–1667 (May, 1993).*

Gold et al., "Adenosine Triphosphate–Derived Nucleotide Formation in the Presence of Ethanol," *Biochemical Pharmacology*, 25, 1825–1830 (Aug. 15, 1976).*

Romanowski et al. (II), Adsorption of Plasmid DNA to Mineral Surfaces and Protection Aganist DNase I, *Applied and Environmental Microbiology*, 57(4), 1057–1061 (Apr., 1991).* van der Pol, et al. (1994) Ordering of Intercalated Water and Carbonate Anions in Hydrotalcite. An NMR Study. Journal of Physical Chemistry vol. 98, p. 4050–4054.

Taylor, H.F.W. (1973) Crystal structures of some double hydroxide minerals. Mineralogical Magazine, vol. 39, No. 304; p. 377–389 (Dec., 1993).

Yun, S.K., et al. (1996) Layered Double Hydroxides Intercalated by Polyoxometalate Anions with Keggin ($\alpha$–$H_2W_{12}O_{40}^{6-}$), Dawson ($\alpha P_2W_{18}O_{62}^{6-}$), and Finke ($Co_4(H_2O)_2\ (PW_9O_{34})_2^{10-}$) Structures. Inorg. Chem, 35, 6853–6860.

* cited by examiner

*Primary Examiner*—Gary Geist
*Assistant Examiner*—L E Crane
(74) *Attorney, Agent, or Firm*—Knobbe, Martens, Olson & Bear, LLP

(57) ABSTRACT

Disclosed is a bio-inorganic hybrid composite for retaining and carrying bio-materials with stability and reversible dissociativity, represented by the following chemical Formula I and a method for preparing the same. The bio-inorganic hybrid composite is prepared by (a) coprecipitating with an alkaline material an aqueous solution comprising a bivalent metal (M(II)) and a trivalent metal (N(III)) at a molar ratio satisfying the condition of $\frac{1}{5} \leq b/(a+b) \leq \frac{1}{2}$ wherein a and b represent a mole number of M and N, respectively, to form a stable layered double hydroxide in which anions are intercalated and (b) subjecting the intercalated anions to ion exchange reaction with a bio-material to compensate for layer charges of the layered double hydroxide. This composite is harmless to the body and artificially controls the appropriate expression of the bio-material retained therein.

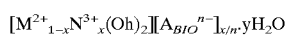

$$[M^{2+}{}_{1-x}N^{3+}{}_x(Oh)_2][A_{BIO}{}^{n-}]_{x/n} \cdot yH_2O \qquad [I]$$

wherein,

M is a bivalent metal cation;

N is a trivalent metal cation;

$A_{BIO}$ is an anionic bio-material with n charges;

x is a rational number between 0 to 1; and y is a positive number.

16 Claims, 7 Drawing Sheets

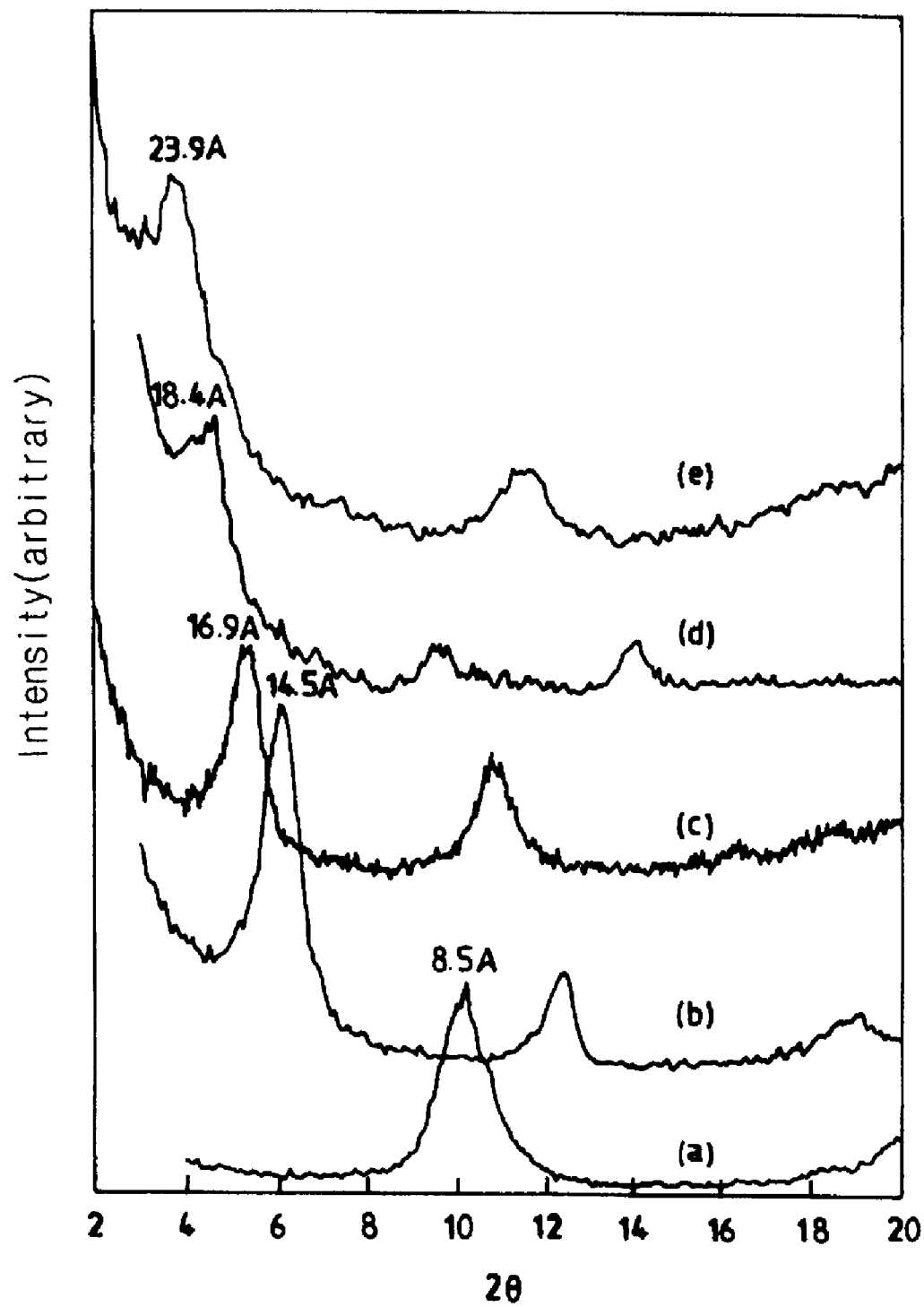
[Fig. 1]

[Fig. 2]
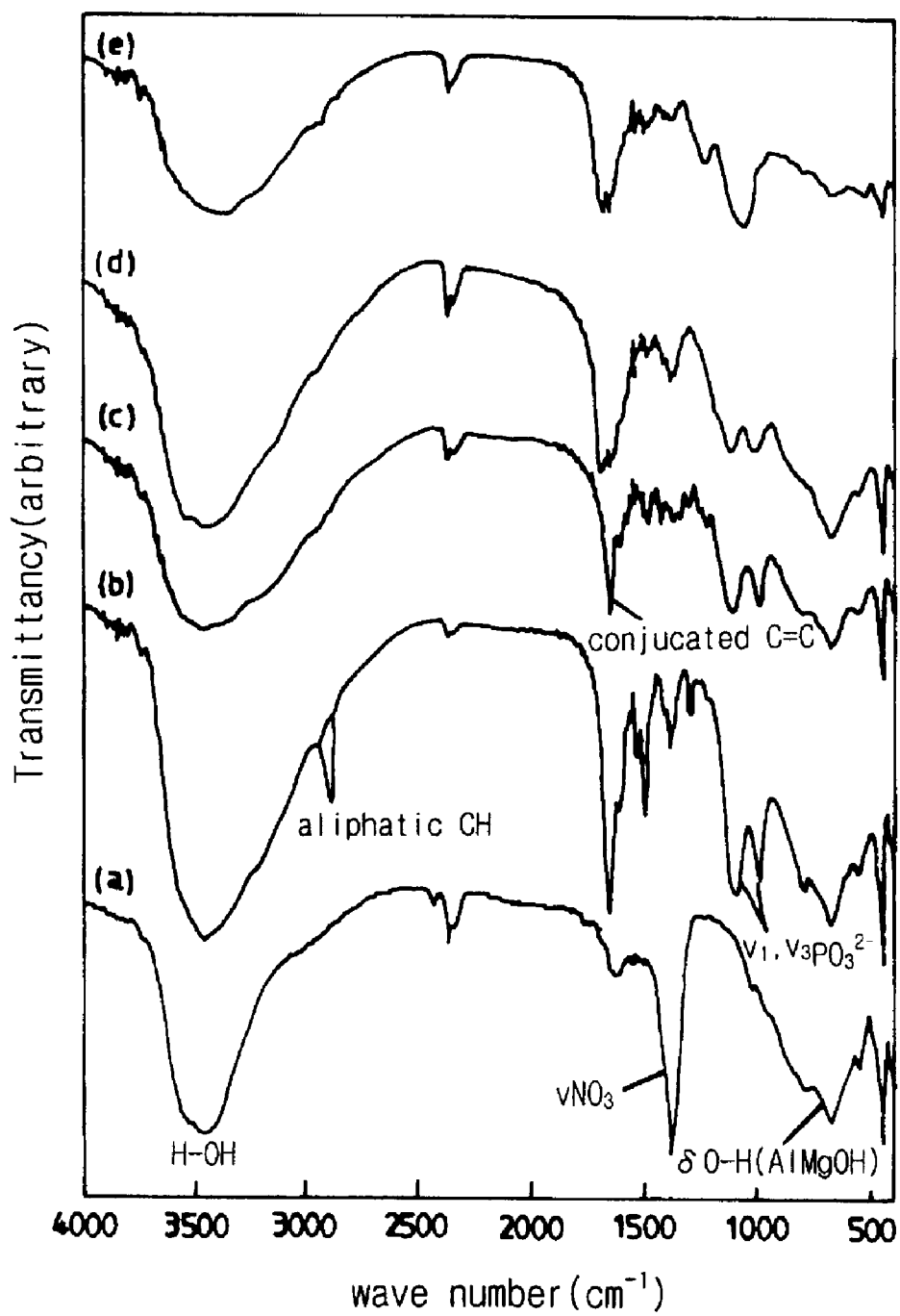

[Fig. 3]
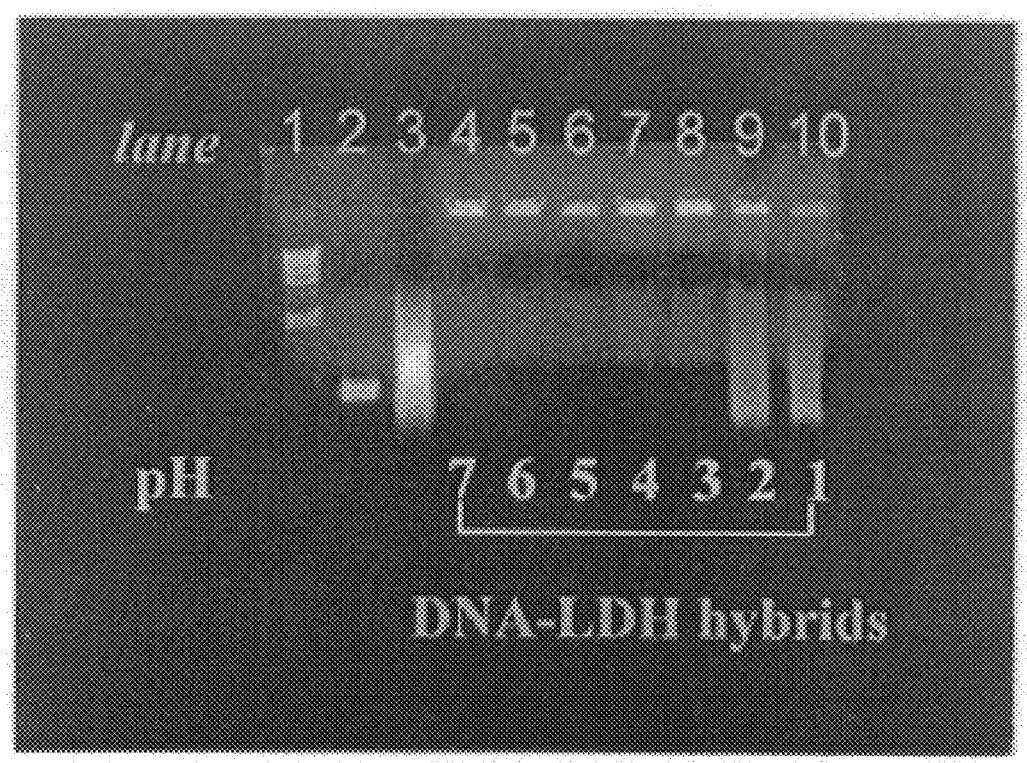

[Fig. 4]
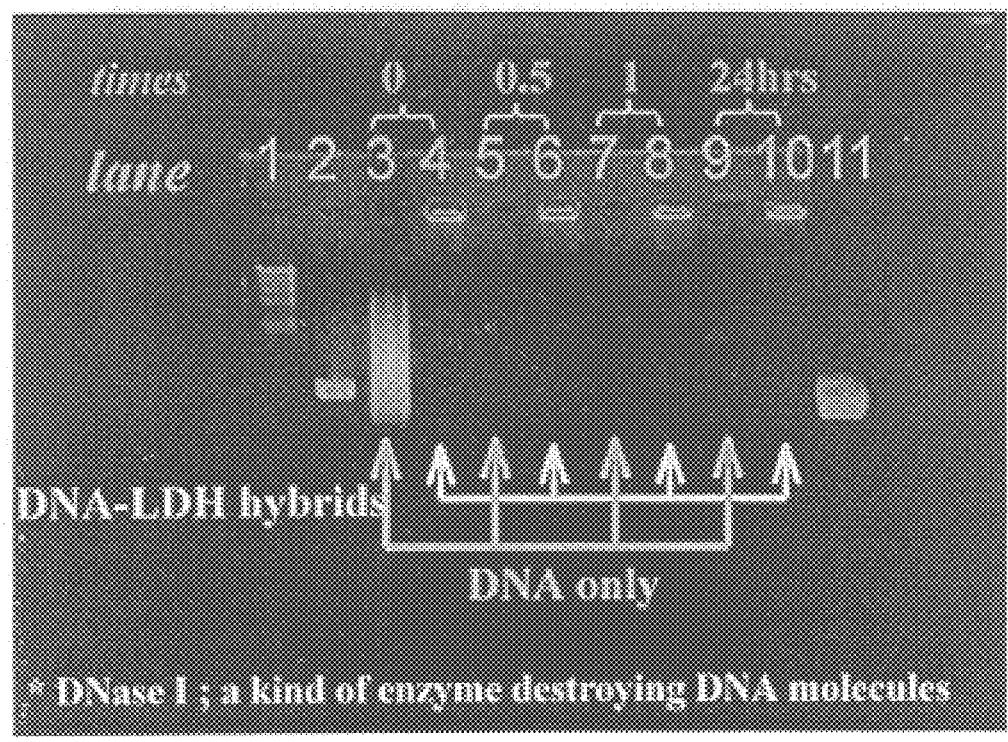

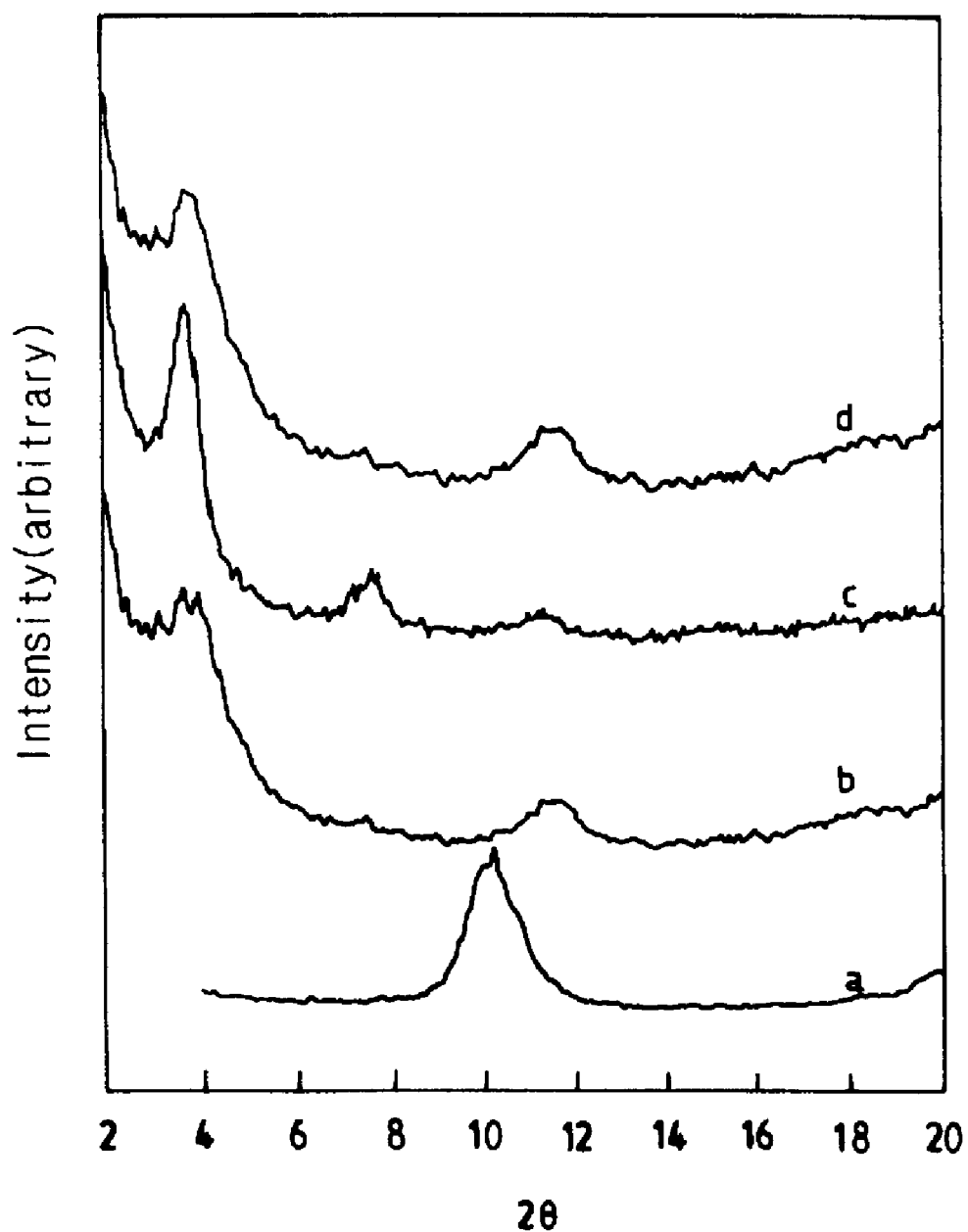
[Fig. 5]

[Fig. 6]
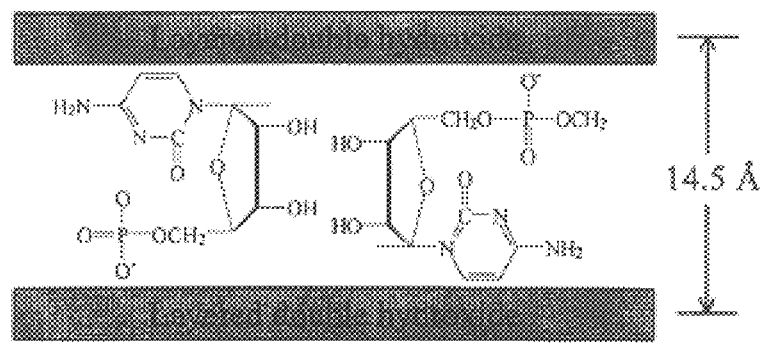
(a) CMP intercalated LDH
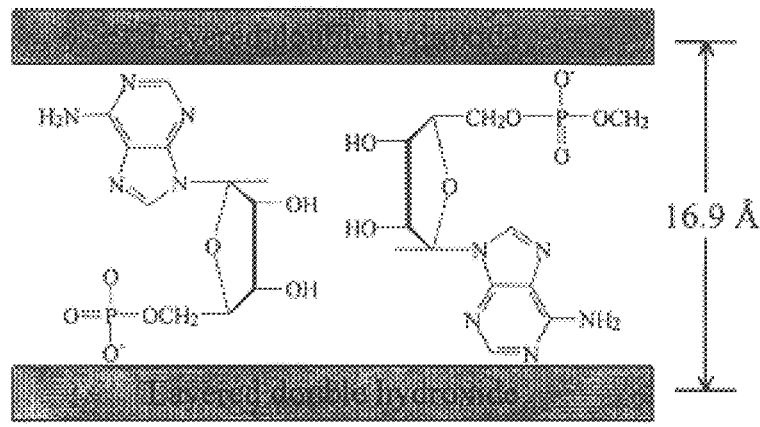
(b) AMP intercalated LDH
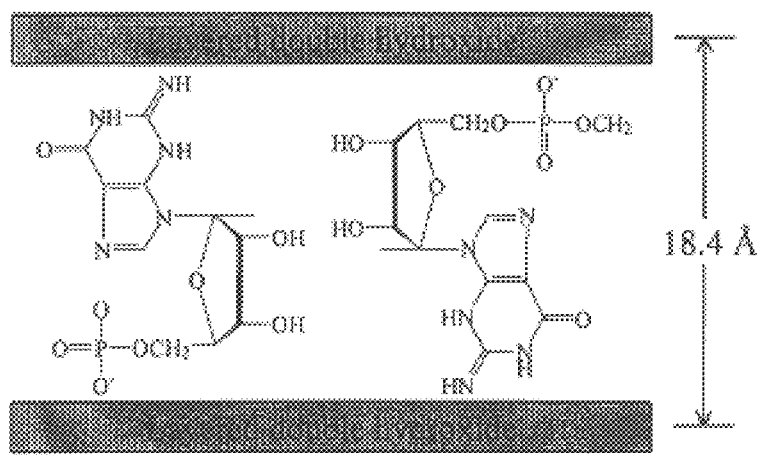
(c) GMP intercalated LDH

[Fig. 7]
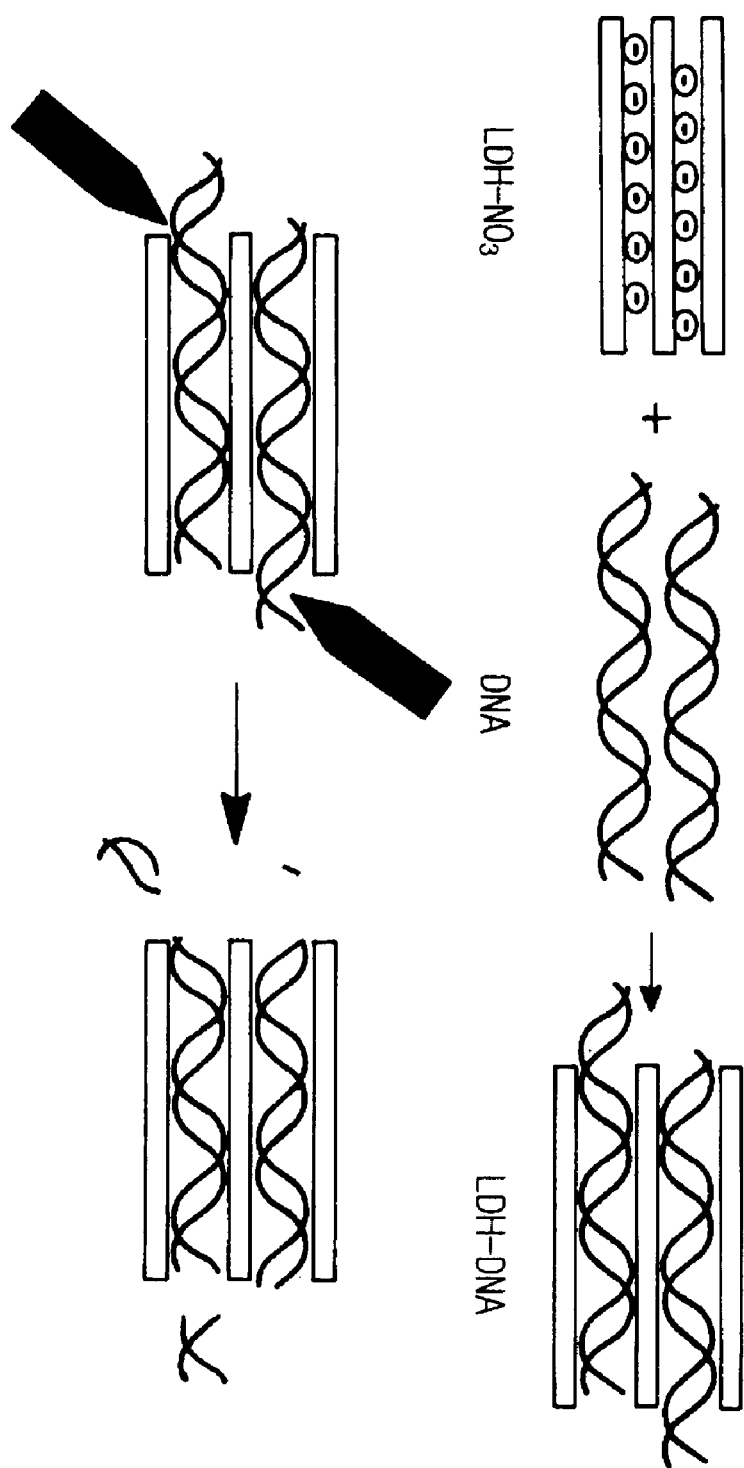

US 6,329,515 B1

BIO-INORGANIC COMPOUND CAPABLE OF STABLE, SOLID-STATE STORAGE OF GENES AND PREPARATION THEREOF

BACKGROUND OF THE INVENTION

The present invention relates to a bio-inorganic hybrid composite which is able to retain and carry bio-materials with stability and reversible dissociativity. Also, the present invention is concerned with a method for preparing such a bio-inorganic hybrid composite.

Generally, most inorganic compounds having lamellar structures, such as aluminosilicate, metal phosphate, etc, have a feature of being able to retain various materials in their interstices. In this regard, a variety of functional guest chemical species can be introduced into the interstices by subjecting the metal ions composing lattice layers to isomorphorous substitution to generate layer charges or modifying the lamellar in such a way that it is provided with physical and chemical absorptivity. Also, it is well known that the pore sizes of porous inorganic compounds, such as crosslink clay, MCM-41, etc, are controlled to physically adsorb selective sizes of molecules. Layered double hydroxides (hereinafter referred to as "LDH"), which are kinds of the inorganic compounds having lamellar structures, are called anionic clays, consisting of positively charged metal hydroxide layers between which anions counterbalancing the positive charges and water are intercalated.

As a rule, these composites are represented by the following chemical Formula:

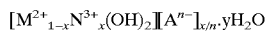

wherein,

M is a bivalent metal cation, selected from alkaline earth metals or transition metals, such as $Mg^{2+}$, $Ni^{2+}$, $Cu^{2+}$, $Zn^{2+}$ and the like, N is a trivalent metal cation, selected from transition metals, such as $Al^{3+}$, $Cr^{3+}$, $Fe^{3+}$, $V^{3+}$, $Ga^{3+}$ and the like, A is an anionic chemical species with n charges, such as $NO_3^-$, $CO_3^{2-}$, $Cl^-$, $SO_4^{2-}$, metalate, anions of organic acids, etc, x is a rational number between 0 to 1; and y is a positive number.

The layer charge densities of the composites can be controlled by changing the metal ratios according to x. Various anions, denoted by A in the LDH, can be easily introduced between the metal hydroxide layers through ion exchange reaction and coprecipitation.

LDH and their derivatives, which are of technical importance in catalytic reactions, are put into spotlight as lamellar nano-composites useful in various fields, including separation technology, optics, medical science, and engineering, and active research has been directed to the composites of interest. For example, hydrotalcite, a mineral name for the compounds based on magnesium and aluminum with similar structures to those of LDH, represented by $[Mg_3Al(OH)_8]^+$ $[0.5CO_3 \cdot mH_2O]^-$, was investigated for the structure of intercalated carbonate anions and water by use of $^1H$ and $^{13}C$-NMR ["Ordering of intercalated water and carbonate anions in hydrotalcite-An NMR study" Journal Physical Chemistry, 1994, 98, 4050–4054]. A synthesis method for crosslinking precursors of the $Mg_3Al$ LDH intercalated with hydroxides and adipate through ion exchange reaction with the aid of polyoxometalate $(P_2W_{18}O_{62}^{6-}$ or $Co_4(H_2O)_2$ $(PW_9O_{34})_2^{10-})$ and assay results for the structural and thermal properties of the resulting composites are reported in ["Layered double hydroxides intercalated by polyoxometalate anions with keggin ($\alpha$-$H_2W_{12}O_{40}^{6-}$), dawson ($\alpha$-$P_2W_{18}O_{62}^{6-}$), and finke $(Co_4(H_2O)_2(PW_9O_{34})_2^{10-})$ structures", Inorganic Chemistry, 1996, 35, 6853–6860]. Structural properties of some LDH are introduced, along with kinds and structures of possible metal cations and common intercalated anions in ["Crystal structures of some double hydroxide minerals", Mineralogical Magazine, 1973, 39[304], 377–389]. A survey of LDH and their derivatives, including their historical backgrounds, possible-components (e.g., kinds of metal cations and intercalated anions), structural properties, and applicability is also found in ["Hydrotalcite-type anionic clays: Preparation, Properties and Applications", catalysis Today, 1991, 11, 173–301].

Being useful as gene carriers, bacteria or cationic liposomes have a feasible possibility of causing side effects owing to their own toxicity and a problem of eliciting immune responses and showing poor expression rates.

Therefore, there remains a need for a structure for retaining and carrying bio materials.

SUMMARY OF THE INVENTION

Based on the fact that genetic materials have a structural property of being negatively charged owing to phosphoric ions, the present invention has an object of preparing a bio-inorganic hybrid composite by intercalating genetic materials in interstices of LDH through anion exchange. LDH is dissolved in acidic conditions, but remains stable in neutral and alkaline conditions. This attribute allows genes or bio materials to be put into or taken from LDH, freely, thereby making it possible for LDH to function as a preserver and carrier for genes or other bio materials. In addition, the bio-inorganic hybrid composite according to the present invention has significant advantages over conventional bio-material carriers, e.g., bacteria or cation liposomes, in that the bio-inorganic hybrid composite is composed of metal hydroxides harmless to the body and artificially controls the appropriate expression of the genetic materials retained therein.

The present invention has significance in that it is the first trial to make metal hydroxides used as a preserver and carrier for genes and bio-materials in the world.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows X-ray diffraction spectra for (a) LDH, (b) CMP-LDH, (c) AMP-LDH, (d) GMP-LHD, and (e) DNA-LDH;

FIG. 2 shows IR spectra for (a) LDH, (b) CMP-LDH, (c) AMP-LDH, (d) GMP-LHD, and (e) DNA-LDH;

FIG. 3 is a photograph showing an electrophoretic result after DNA-LDH composites are run on an agarose gel in various pH conditions;

FIG. 4 is a photograph showing an electrophoresis result obtained after the DNA-LDH composites are treated with Dnase I for various periods of time;

FIG. 5 shows X-ray diffraction spectra for (a) LDH (NO$_3$ form), (b) ATP-LDH, (c) RNA-LDH, and (d) DNA-LHD;

FIG. 6 is a schematic diagram showing the intercalation state of bio-materials in LDH, (a) CMP-LDH, (b) AMP-LDH and (c) GMP-LDH; and FIG. 7 is a schematic diagram showing a forming procedure of a DNA-LDH hybrid composite according to the present invention, including intercalation and DNase I treatment.

DETAILED DESCRIPTION OF THE INVENTION

Details are given of the present invention, below.

The present invention provides a bio-inorganic hybrid composite for retaining and carrying genes and bio-materials with stability and reversible dissociativity, which is prepared by subjecting LDH to ion exchange with bio-materials. The bio-inorganic hybrid composite is represented by the following chemical Formula I:

$$[M^{2+}_{1-x}N^{3+}_{x}(OH)_2][A_{BIO}{}^{n-}]_{x/n} \cdot yH_2O \quad [I]$$

wherein,

M is a bivalent metal cation;

N is a trivalent metal cation;

$A_{BIO}$ is an anionic bio-material with n charges;

x is a rational number between 0 to 1; and y is a positive number.

Particularly, all alkaline earth metals and transition metals are available as M and N for which Mg and Al are preferably substituted, respectively.

As for $A_{BIO}$, its negative charges compensate for the layer charges of the hybrid composite and it may be nucleoside-5'-monophosphate, nucleoside-5'-triphosphate, or a gene material with a size of 500–1,000 bp.

A nucleoside-5'-monophosphate is a repeating unit composing a gene material. It has a nucleoside moiety consisting of a base and a sugar to which a phosphate group is attached in ester linkage. The phosphate group is negatively charged in aqueous solutions, thus providing the genetic materials, divided largely into DNA and RNA, with negative charges.

The bio-inorganic hybrid composite of the chemical Formula I is prepared as follows.

First, the metal cations, M(II) and N(III) are mixed in an aqueous solution at a molar ratio satisfying the condition of $\frac{1}{5} \leq b/(a+b) \leq \frac{1}{2}$ wherein a and b represent a mole number of M and N, respectively. Then, the aqueous salt solution is coprecipitated using an alkaline material, to cause the isomophorous substitution of N(III) for M(II) of a brucite $(Mg(OH)_2)$ structure, thereby leading to an induction of excess positive charges in lattice layers. To compensate for the generated charges, anions are intercalated from the aqueous solution in the layers to form stable LDH with intercalation of anions. The intercalated anions can be replaced with some bio-materials with negative charges, e.g., nucleoside-5'-monophosphate, nucleoside-5'-triphosphate, and DNA or RNA with a stretch of 500–1,000 bp, to give the bio-inorganic hybrid composite of the chemical Formula I.

In the present invention, the intercalation of negatively charged bio-materials in the interstices of LDH is stably maintained by the electrostatic attraction between two oppositely charged materials. The genetic materials intercalated, if required, can be reclaimed as being intact through ion exchange reaction or selective dissolution.

The LDH used in the present invention is composed of metals nontoxic to the body. Particularly when magnesium and aluminum are used, that is, when the M and N in the chemical Formula I are Mg and Al, respectively, the resulting LDH are easily dissolved in acidic conditions and the ionized metals are known to be eliminated from the body through appropriate metabolism. In fact, hydroxides of magnesium and aluminum are widely used in antacids for protecting stomach walls. In addition, because metals are different in the solubility in acid conditions from one to another, the bio-inorganic hybrid composite of the present invention can be controlled in its dissolution through appropriate combinations of bivalent metals and trivalent metals, so that the expression time of the gene intercalated therein can be controlled.

A better understanding of the present invention may be obtained in light of the following examples which are set forth to illustrate, but are not to be construed to limit the present invention. In the following examples, bio-inorganic hybrid composites according to the present invention were assayed for properties as follows:

Assay Condition

1) Assay Using IR Spectrum

Sample pretreatment: Mixed with KBr and compressed into a disc.

Measuring instrument: Spectrophotometer from Perkin-Elmer

Measuring frequency range: 400–4,000 $cm^{-1}$

2) Assay Using Electrophoresis i) Assay for pH

Sample pretreatment: pH controlled with HCl and electrophoresed at room temperature for 1 hour.

Measuring method: Dyed with ethidium bromide and run on 0.7% agarose gel under an electric field.

Measurement Range: pH 7 to 1.

ii) Assay for Dnase I

Sample pretreatment: Treated with Dnase I at room temperature for a period of 0.5, 1 and 24 hours. Treated with Dnase I at room temperature for 1 hour, quenched in a solution (0.2 M NaCl, 40 mM EDTA, 1% SDS), and treated at pH 2 for 1 hour.

Measuring method: Electrophoresed on 0.7% agarose gel.

EXAMPLE I $Mg(NO_3)_2$ and $Al(NO_3)_3$ were combined at such an amount that the mole ratio of Mg(II) to Al(III) was 3:1. To this combined solution, a solution of 0.2 M NaOH in water was dropwise added, causing coprecipitation. The precipitates thus obtained were washed and centrifuged to synthesize LHD intercalated by nitrate ($MgAl(NO_3)$—LDH, hereinafter referred to as $NO_3$—LDH). The whole procedure was conducted in a nitrogen atmosphere to prevent the $NO_3$—LDH from being contaminated with $CO_2$.

The $NO_3$—LDH was analyzed through X-ray diffraction and infrared spectrometry whose results are shown in FIGS. 1 (spectrum a) and 2 (spectrum a), respectively.

To a suspension of the $NO_3$—LDH in water (1 mg/1 ml $H_2O$), a solution of 10 mg of cytidine-5'-monophosphate (CMP) in boiled water was added, and they were allowed to undergo ion exchange reaction with each other for 24 hours in an incubating bath maintained at 50° C. After completion of the ion exchange reaction, the product was washed three times with boiled water to completely remove excess phosphate and dried in an oven at 70° C.

Spectrometric analysis was conducted for the product with X-ray and infrared whose results are shown in FIGS. 1 (spectrum b) and 2 (spectrum b), respectively.

As apparent from the spectra of FIGS. 1 and 2, the interlayer distance in the $NO_3$—LDH composite was found to correspond to the size of CMP and the absorption IR peaks read were coincident with characteristic functional groups of CMP. Taken together, these data demonstrate that CMP is stably intercalated in the interstices of the LDH. Based on this result, a possible array of CMPs in the interstices of the LDH is suggested in FIG. 6 at panel a.

EXAMPLE II

The same procedure as in Example I was repeated using adenosin-5'-monophosphate (AMP).

The $NO_3$—LDH suspension (1 mg/1 ml $H_2O$) obtained in Example I was added to a solution of 10 mg of AMP in boiled water, and they were allowed to undergo ion exchange reaction with each other for 24 hours in an incubating bath maintained at 50° C. After completion of the ion exchange reaction, the product was washed three times with boiled water to completely remove excess phosphate and dried in an oven at 70° C.

Spectrometric analysis was conducted for the product with X-ray and infrared whose results are shown in FIGS. 1 (spectrum c) and 2 (spectrum c), respectively.

As apparent from the spectra of FIGS. 1 and 2, the interlayer distance in the $NO_3$—LDH composite was found to correspond to the size of AMP and the absorption IR peaks read were coincident with characteristic functional groups of AMP, demonstrating that AMP was stably intercalated in the interstices of the LDH. Based on this result, a possible array of AMPs in the interstices of the LDH is suggested in FIG. 6 at panel b.

EXAMPLE III

The same procedure as in Example I was repeated using guanidine-5'-monophosphate (GMP).

The $NO_3$—LDH suspension (1 mg/1 ml $H_2O$) obtained in Example I was added to a solution of 10 mg of GMP in boiled water, after which they were allowed to undergo ion exchange reaction with each other for 24 hours in an incubating bath maintained at 50° C. After completion of the ion exchange reaction, the product was washed three times with boiled water to completely remove excess phosphate and dried in an oven at 70° C.

Spectrometric analysis was conducted for the product with X-ray and infrared whose results are shown in FIGS. 1 (spectrum d) and 2 (spectrum d), respectively.

As apparent from the spectra of FIGS. 1 and 2, the interlayer distance in the $NO_3$—LDH composite corresponded to the size of AMP and the absorption IR peaks read were coincident with characteristic functional groups of AMP, demonstrating that GMP was stably intercalated in the interstices of the LDH. Based on this result, a possible array of GMPs in the interstices of the LDH is suggested in FIG. 6 at panel c.

EXAMPLE IV

To a suspension of the $NO_3$—LDH in water (1 mg/1 ml $H_2O$) obtained in Example I, a solution of 10 mg of Herring testes DNA (hereinafter referred to as DNA) in boiled water was added, and they were allowed to undergo ion exchange reaction with each other for 24 hours in an incubating bath maintained at 50° C. After completion of the ion exchange reaction, the product was washed three times with boiled water to completely remove excess DNA and dried in an oven at 70° C.

Spectrometric analysis was conducted for the product with X-ray and infrared whose results are shown in FIGS. 1 (spectrum e) and 2 (spectrum e), respectively.

As apparent from the spectra of FIGS. 1 and 2, the interlayer distance in the $NO_3$—LDH composite was found to correspond to the size of DNA and the absorption IR peaks read were coincident with characteristic functional groups of DNA. Taken together, these data demonstrate that DNA is stably intercalated in the interstices of the LDH.

With reference to FIG. 3, there is an electrophoresis result which gives information regarding the dissociation degrees of the DNA-LDH composite in dependence on pH. On lane 1 was run a DNA marker (λ/HindIII) which contained DNA fragments with sizes of 23.1, 9.4, 6.5, 4.3, 2.3 and 2.0 kb. The DNA-LDH composites were electrophoresed on lanes 4 to 10 after being treated at pH 7, 6, 5, 4, 3, 2 and 1, respectively. Also, a marker 500 bp in length and the DNA used in preparing the composite were run on lanes 2 and 3, respectively.

As seen in FIG. 3, no trails are found on lanes 4 to 8, indicating that the negative charges of DNA are compensated in the interstices of the LDH. On the contrary, traces electrophoresed in an electric field are found on lanes 9 and 10, both. Based on this electrophoresis analysis, it is believed that the layers of LDH collapse at less than pH 3, particularly at pH 2 or less, so that the DNA confined between the layers is released. In recognition of the moving to the same distance as in the control DNA running on lane 3 upon electrophoresis, DNAs on lanes 9 and 10 are believed to be preserved intact within the LDH.

With reference to FIG. 4, there is an electrophoresis result which gives information regarding the preservation of DNA in the composite through DNase I treatment. The DNA markers run on lanes 1, 2 and 3 were the same as in Example I. Along with intact DNA-LDH, which was not treated with DNases, on lane 4, only DNAs were electrophoresed on lane lanes 5, 7 and 9 after being treated with DNase I for 0.5, 1 and 24 hours, respectively, while the DNA-LDH composites treated with DNase I for 0.5, 1 and 24 hours were allowed to run in an electric field on lanes 5, 7 and 9, respectively. The DNA electrophoresed on lane 11 came from the DNA-LDH composite after it was treated with DNase I for 1 hour and then, with a solution to quench the enzyme and finally, allowed to stand for 1 hour at pH 2.

The electrophoresis patterns on lanes 6, 8 and 10, as seen in FIG. 4, are similar to that on lane 4, indicating that the DNA intercalated in the interstices of the composite are maintained intact. This result is quite contrary to the electrophoresis results on lanes 5, 7 and 9, which were obtained after DNAs alone were treated in the same conditions as that for lane 4. Confirming the result of lanes 6, 8 and 10, the electrophoresis pattern on lane 11, which was obtained after the same sample as on lane 8 was treated to quench the DNase I, allowed stand at pH 2 for 1 hour to release the DNA from the interstices of the LDH and electrophoresed, showed that the DNA within LDH was preserved intact. The procedure in which DNA is intercalated in the interstices of LDH, treated with DNase I, and preserved intact is illustrated in FIG. 7. Therefore, the electrophoresis data of FIG. 4 demonstrate that the LDH according to the present invention is a very stable carrier for DNA and other bio-materials and has a characteristic of being easily dissociated.

EXAMPLE V

The $NO_3$—LDH suspension (1 mg/1 ml $H_2O$) obtained in Example I was added to a solution of 10 mg of ATP in boiled water, and they were allowed to undergo ion exchange reaction with each other for 24 hours in an incubating bath maintained at 50° C. After completion of the ion exchange reaction, the product was washed three times with boiled water to completely remove excess phosphate and dried in an oven at 70° C.

X-ray diffraction analysis data for the product are given in FIG. 5 (spectrum b). As apparent from the diffraction data, the 001 peak, which is indicative of interlayer distances in a solid, was moved toward a lower angle compared with the starting material, indicating that an expansion occurs between layers. Because the decreased angle extent was found to correspond to the thickness of ATP, it was demonstrated to be stabilized in LDH.

EXAMPLE VI

The NO$_3$—LDH suspension (1 mg/1 ml H$_2$O) obtained in Example I was added to a solution of 10 mg of an antisense single strand of RNA in boiled water, and they were allowed to undergo ion exchange reaction with each other for 24 hours in an incubating bath maintained at 50° C. After completion of the ion exchange reaction, the product was washed three times with boiled water to completely remove excess phosphate and dried in an oven at 70° C.

X-ray diffraction analysis data for the product are given in FIG. 5 (spectrum c). As apparent from the diffraction data, the 001 peak, which is indicative of interlayer distances in a solid, was moved toward a lower angle compared with the starting material, indicating that an expansion occurs between layers. Because the decreased angle extent was found to correspond to the thickness of ATP, it was demonstrated to be stabilized in LDH.

As described hereinbefore, the present invention provides a bio-inorganic hybrid composited which can preserve and carry genes and is nontoxic to the body and easily dissociated.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A bio-inorganic compound for storage of bio-materials with stability and reversible dissociativity, comprising the following chemical Formula I:

$$[M^{2+}_{1-x}N^{3+}x(OH)_2][A_{BIO}{}^{n-}]_{x/n} \cdot yH_2O \qquad [I]$$

wherein,

M is a bivalent metal cation;

N is a trivalent metal cation;

A$_{BIO}$ is an anionic bio-material with n charges selected from the group consisting of: a nucleoside-5'-monophosphate, a nucleoside-5'-triphoshate, DNA and RNA;

X is a rational number between 0 to 1; and

Y is a positive number.

2. The bio-inorganic compound of claim 1, wherein the M represents Mg and the N represents Al.

3. A method for preserving and recovering bio-materials using a bio-inorganic compound, represented by the following chemical Formula I:

$$[M^{2+}_{1-x}N^{3+}x(OH)_2][A_{BIO}{}^{n-}]_{x/n} \cdot yH_2O \qquad [I]$$

wherein,

M is a bivalent metal cation;

N is a trivalent metal cation;

A$_{BIO}$ is an anionic bio-material with n charges selected from the group consisting of: a nucleoside-5'-monophosphate, a nucleoside-5'-triphosphate, DNA and RNA;

X is a rational number between 0 to 1; and

Y is a positive number, said method comprising:
(a) intercalating the bio-materials to form the bio-inorganic compound according to claim 1; and
(b) reclaiming the bio-material by treating the bio-inorganic compound with an acidic reagent.

4. A method as set forth in claim 3, wherein the M and the N represent Mg and Al, respectively, and the acidic reagent has a pH of 3 or less.

5. The method of claim 3 wherein said intercalation takes place for about 24 hours at about 50° C.

6. The method of claim 3, wherein said the acidic reagent has a pH less than or equal to 3.0.

7. The method of claim 3, wherein said the acidic reagent has a pH less than or equal to 2.0.

8. The method of claim 3 further comprising washing the bio-material at least one time with water or buffer.

9. The method of claim 3 further comprising; drying the bio-inorganic compound.

10. The method of claim 9 wherein said drying occurs at about 70° C.

11. A method for preparing a bio-inorganic compound represented by the following chemical Formula I:

$$[M^{2+}_{1-x}N^{3+}x(OH)_2][A_{BIO}{}^{n-}]_{x/n} \cdot yH_2O \qquad [I]$$

wherein,

M is a bivalent metal cation;

N is a trivalent metal cation;

A$_{BIO}$ is an anionic bio-material with n charges selected from the group consisting of: a nucleoside-5'-monophosphate, a nucleoside-5'-triphosphate, DNA and RNA;

X is a rational number between 0 to 1; and

Y is a positive number, comprising the steps of:
(a) coprecipitating with an alkaline material an aqueous solution comprising a bivalent metal (M(II)) and a trivalent metal (N(III)) at a molar ration satisfying the condition of $1/3 \leq b/(a+b) \leq 1/2$ wherein a and b represent a mole number of M and N, respectively, to form a stable layered double hydroxide in which anions are intercalated; and
(b) adding the bio-material to the stable layered double hydroxide thus allowing the intercalated anions to go through an ion exchange reaction with the bio-material, creating a bio-inorganic compound.

12. The method of claim 11, wherein the M represents Mg and the N represents Al.

13. The method of claim 11 wherein said ion-exchange reaction is allowed to proceed for about 24 hours at about 50° C.

14. The method of claim 11 further comprising washing at least one time with water or buffer.

15. The method of claim 11 further comprising: drying the inorganic hybrid composite.

16. The method of claim 11 wherein said drying occurs at about 70° C.

* * * * *

UNITED STATES PATENT AND TRADEMARK OFFICE
CERTIFICATE OF CORRECTION

PATENT NO.    : 6,329,515 B1
DATED         : December 11, 2001
INVENTOR(S)   : Jin Ho Choy, Seo Young Kwak and Jong Sang Park It is certified that error appears in the above-identified patent and that said Letters Patent is hereby corrected as shown below:

Column 8,
Line 43, "at a molor ration" should be change to -- at a molor ratio --

Signed and Sealed this

Eleventh Day of March, 2003

JAMES E. ROGAN
*Director of the United States Patent and Trademark Office*